United States Patent [19]

Pathak et al.

[11] Patent Number: 6,156,531
[45] Date of Patent: Dec. 5, 2000

[54] CROSS-LINKING TISSUE WITH A COMPOUND HAVING A $C_8$ TO $C_{40}$ ALIPHATIC CHAIN

[75] Inventors: C. P. Pathak; Mark A. Moore, both of Austin, Tex.

[73] Assignee: Sulzer Carbomedics Inc., Austin, Tex.

[21] Appl. No.: 09/119,205

[22] Filed: Jul. 20, 1998

[51] Int. Cl.[7] .............................. G01N 1/30; C12N 11/06; A61K 38/17; C07K 1/00; C07K 17/06

[52] U.S. Cl. ...................... 435/40.5; 435/1.1; 435/40.52; 435/181; 530/356; 530/402; 530/816

[58] Field of Search .............................. 435/40.5, 40.52, 435/181, 1.1; 530/356, 402, 816

[56] References Cited

U.S. PATENT DOCUMENTS

| | | | |
|---|---|---|---|
| 4,035,506 | 7/1977 | Lucas et al. | 424/303 |
| 4,838,888 | 6/1989 | Nashef | 623/2 |
| 5,098,960 | 3/1992 | Frautschi | 525/359.3 |
| 5,147,514 | 9/1992 | Mechanic | 204/157.68 |
| 5,215,541 | 6/1993 | Nashef et al. | 8/94.11 |
| 5,263,992 | 11/1993 | Guire | 623/66 |
| 5,332,475 | 7/1994 | Mechanic | 204/157.68 |
| 5,447,536 | 9/1995 | Girardot et al. | 8/94.11 |
| 5,476,516 | 12/1995 | Seifter et al. | 8/94.11 |
| 5,549,666 | 8/1996 | Hata et al. | 623/2 |
| 5,645,587 | 7/1997 | Chanda et al. | 623/11 |
| 5,697,972 | 12/1997 | Kim et al. | 623/2 |
| 5,769,780 | 6/1998 | Hata et al. | 600/36 |
| 5,931,969 | 8/1999 | Carpentier et al. | 8/94.11 |
| 5,958,669 | 9/1999 | Ogle et al. | 435/1.1 |

OTHER PUBLICATIONS

Khor, Eugene, Biomaterials, vol. 18, No. 2, 1997, pp. 95–105.
Broom, N. D., "The Stress/Strain and Fatigue Behaviour of Glutaralydehyde Preserved Heart–Valve Tissue", J. Biomechanics, 1997, vol. 10, pp. 707–724.
Gendler, E., "Toxic Reactions Evoked by Glutaralydehyde–Fixed Pericardium and Cardiac Valve Tissue Bioprosthesis",Journal of Biomedical Materials Research, vol. 18, 727–736 (1984).
Girardot, M.N., et al., "Alpha–Aminoleic Acid, A New Compound,Prevents Calcification of Bioprostheticheart Valves", The 17th Annual Meeting of the Society for Biomaterials, May 1–5, 1991, p. 114.
Girardot, M.N., et al., "Development of the AOA Process as Antimineralization Treatment for Bioprosthetic Heart Valves", The 19th Annual Meeting of the Society for Biomaterials, Apr. 28–May 2, 1993, p. 266.
Girardot, M.N., et al., "Effect of AOA on Glutaralydehyde–Fixed Bioprosthetic Heart Valve Cusps and Walls: Binding and Calcification Studies", The International Journal of Artificial Organs, vol. 17, No. 2, 1994, pp. 76–82.
Girardot, M. N., et al., "Role of Glutaraldehyde in Calcification of Porcine Heart Valves: Comparing Cusp and Wall", Journal of Biomedical Materials Research, vol. 29, 1995, pp. 793–801.

Golomb, G., et al., "The Role of Glutaraldehyde–Induced cross–Links in Calcification of Bovine Pericardium Used in Cardiac Valve Bioprostheses",AJP, Apr. 1987, vol. 127, No. 1, pp. 122–130.
Gott, J. P., et al., "Calcification of Porcine Valves: A Successful New Method of Antimineralization",Ann Thorac Surg, 1992, vol. 53, pp. 207–216.
Thubrikar, M. J., et al., "Role of Mechanical Stress in Calcification of Aortic Bioprosthetic Valves",J Thorac Cardiovasc Surg, vol. 86, 1983, pp. 115–125.
Myers, D. J., et al., "Biocompatibility Testing of Stentless Heart Valves Treated With 2–Amino Oleic Acid, A New Antimineralization Agent", The International Journal of Artificial Organs, vol. 16, No. 6, 1993, p. 453.
Munro, M. S., et al., "Alkyl Substituted Polymers with Enhanced Albumin Affinity", Trans Am Soc Artif Intern Organs, 1981, vol. 27, 1981, pp. 499–503.
Moczar, M., et al., "Deterioration of Bioprosthetic Heart Valves",ASAIO Journal 1992, pp. M697–M701.
Magilligan, D. J., "The Future of Bioprosthetic Valves", Trans Am Soc Artif Intern Organs, vol. 34, 1988, pp. 1031–1032.
Levy, R. J., et al., "Bioprosthetic Heart Valve Calcification-:Clinical Features, Pathobiology,and Prospects for Prevention",CRC Critical Reviews in Biocompatibility, vol. 2, Issue 2, pp. 147–187.
Thoma, R. J., "Poly(ether) Urethane Reactivity with Metal–Ion in Calcification and Environmental Stress Cracking", Journal of Biomaterials Applications, vol. 1, Apr. 1987, pp. 449–486.
Goissis, G., et al., "The Chemical Protecting Group Concept Applied in Crosslinking of Natural Tissues with Glutaraldehyde Acetals", Artificial Organs, 22 (3), pp. 210–214.
Eberhart, R. C., "Surface Treatments to Improve the Albumin Affinity and Blood Compatibility of Polymers", Engineering in Medicine and Biology Magazine, Jun. 1989, pp. 26–29.
Parnis, S. M., "Acoustic Spectral Analysis of an Electrohydraulic Artificial Heart (TAH)", ASAIO Journal, vol. 41, No. 1, p. 9.
Wiebe, D., "Glutaraldehyde Release from Vascular Prostheses of Biologic Origin", Surgery (104), 1988, pp. 26–33.
Zilla, P., et al., "Improved Ultrastructural Preservation of Bioprosthetic Tissue", J Heart Valve Dis, vol. 6, No. 5, Sep. 1997, pp. 492–501.

(List continued on next page.)

*Primary Examiner*—David M. Naff
*Attorney, Agent, or Firm*—Timothy L. Scott; Philip S. Lyren; Kenneth S. Barrow

[57] ABSTRACT

Collagen-containing tissue is cross-linked to provide tissue suitable for use in production of bioprosthetic devices. A cross-linking agent is used having an aliphatic component containing about 8 to 40 carbon atoms and two collagen-reactive groups such as isocyanate, epoxy or n-hydroxysuccinimide. The cross-linking agent may be produced by dimerizing fatty acids, and modifying carboxylic acid group of the fatty acids before or after dimerization to contain collagen-reactive groups. The cross-linked tissue has desirable mechanical and biocompatibility features and a reduced susceptibility to calcification.

25 Claims, No Drawings

OTHER PUBLICATIONS

Khor, E., "Methods for the Treatment of Collagenous Tissues for Bioprostheses", Biomaterials, 1997, vol. 18, No. 2, pp. 95–105.

Greene, T. W., et al., "Protectionfor the Carbonylgroup", Protective Groups in Organic Synthesis, pp. 175–223.

Cheung, D. T., et al., "Mechanism of Crosslinking of Proteins by Glutaraldehyde II. Reaction with Monomeric and Polymeric Collagen", Connective Tissue Research, 1982, vol. 10, pp. 201–216.

Nimni, M. E., "A Defect in the Intramolecular and Intermolecular Cross–Linking of Collagen Caused by Penicillamine",The Journal of Biological Chemistry, vol. 243, No. 7, Apr. 10, 1968, pp. 1458–1466.

Carpentier, A., et al., "Biological Factors Affecting Long–Term Results of Valvular Heterografts",Journal of Thoracic and CardiovascularSurgery, vol. 58, No. 4, Oct., 1969, pp. 467–483.

Chvapil, M., et al., "Effect of Collagen Crosslinking on the Rate of Resorption of Implanted Collagen Tubing in Rabbits", vol. 11,1977, pp. 297–314.

Nimni, M. F., et al., "Chemically Modified Collagen: A Natural Biomaterial for Tissue Replacement",Journal of Biomedical Materials Research, vol. 21, 1987, pp. 741–771.

Woodreof, F. A., "Use of Glutara.ldehyde and Formaldehyde to Process Tissue Heart Valves", Processed Tissue Valves, vol. 2, pp. 1–9.

Schoen, F. J., et al., "Cuspal Components in Bioprosthetic Valve Calcification:Elucidation and Modification",Surgery for Heart Valve Disease, 1989, pp. 679–685.

Levy, R. J., et al., "Inhibition by Diphosphonate Compounds of Calcification of Porcine Bioprosthetic Heart Valve Cusps Implanted Subcutaneouslyin Rats", vol. 71, No. 2, Feb. 1985, pp. 349–356.

Webb, C. L., et al., "Al+++ Preincubation Inhibits Calcification of Bioprosthetic Heart Valve Tissue in the Rat Subdermal Model", Trans Am Soc Artif Intern Organs, vol. 34, 1988, pp. 855–859.

Baldwin, M., et al., "Fe3+ Pretreatment Provides Sustained Inhibition of Bioprosthetic Heart Valve Calcification", The 17th Annual Meeting of the Society for Biomaterials,May 1–5, 1991, p. 61.

Bernacca, G. M., et al., "Chemical Modification of Bovine Pericardium and its Effect on Calcification in the Rat Subdermal Model", Biomaterials, 1992, vol. 13, No. 6.

Chanda, J., "Prevention of Calcification of Heart Valve Bioprostheses:An Experimental Study in Rat",Ann Thorac Surg, 1995, 60, S339–S342.

Vesely, I., et al., "The Hybrid Xenograft/Autograft Biopros-thetic Heart Valve: In Vivo Evaluation of Tissue Extraction", Ann Thorac Surg, 1995, 60, S359–S364.

Okoshi, T., et al., "A New Bioprosthetic Cardiac Valve with Reduced Calcification",ASAIO Transactions 1990, 36, pp. M411–M414.

Moore, M. A., et al., "Stabilization of Pericardial Tissue by Dye–Mediated Photooxidation", Journal of Biomedical Materials Research, vol. 28, 1994, pp. 611–618.

Oster, G., et al., "Dye Sensitized Photooxidation",J. Am. Chem. Soc. Oct. 5, 1959, vol. 81, pp. 5095–5099.

Cao, H., et al., "Characterization of Mechanical Properties of Photooxidation Modified Bovine Pericardium",21st Annual Meeting of the Society for Biomaterials, Mar. 18–22, 1995, p. 82.

CROSS-LINKING TISSUE WITH A COMPOUND HAVING A $C_8$ TO $C_{40}$ ALIPHATIC CHAIN

BACKGROUND AND SUMMARY OF THE INVENTION

The present invention relates generally to the field of medical devices for implantation into humans. More particularly, it concerns methods for processing biological tissues for use as bioprosthetic devices.

Bioprostheses are devices derived from processed biological tissues to be used for implantation into humans. The development of such devices originated as an attempt to circumvent some of the clinical complications associated with the early development of the mechanical heart valve, and has since resulted in a rapid proliferation of bioprosthetic devices for a variety of applications. Examples of some of the bioprostheses currently used or under development include heart valves, vascular grafts, biohybrid vascular grafts, ligament substitutes, and pericardial patches.

The primary component of the biological tissues used to fabricate bioprostheses is collagen, a generic term for a family of related extracellular proteins. Collagen molecules consists of three chains of poly(amino acids) arranged in a trihelical configuration ending in non-helical carboxyl and amino termini. These collagen molecules assemble to form microfibrils, which in turn assemble into fibrils, resulting in collagen fibers. The amino acids which make up the collagen molecules contain side groups, including amine (NH2), acid (COOH) and hydroxyl (OH) groups, in addition to the amide bonds of the polymer backbone, all of which are sites for potential chemical reaction on these molecules.

Because collagenous tissues degrade very rapidly upon implantation, it is necessary to stabilize the tissue if it is to be used clinically. Chemical stabilization by tissue cross-linking, also referred to as tissue fixation, has been achieved using bi- and multi-functional molecules having reactive groups capable of forming irreversible and stable intra- and intermolecular chemical bond formation with the reactive amino acid side groups present on the collagen molecules.

Glutaradehyde is a bifunctional molecule capable of reacting under physiological conditions with primary amine groups on collagen molecules. Although it is the most commonly used chemical fixative for biological tissues, there are a number of drawbacks associated with its use in the production of bioprosthetic devices. For example, the long term durability of glutaraldehyde-fixed bioprostheses is not well established, particularly in view of a number of reports of mechanical failures of the tissue at points of high mechanical stress (Broom, 1977; Magilligan, 1988). Another drawback to glutaraldehyde fixation of bioprostheses relates to the depolymerization of the cross-links that has been observed in vivo, resulting in release of toxic glutaraldehyde into the recipient (Moczar et al., 1994; Wiebe et al., 1988; Gendler et al., 1984).

In addition, glutaraldehyde-fixed biprostheses have an undesirable propensity to calcify after implantation. This calcification appears to represent the predominant cause of failure of glutaraldehyde-fixed devices (Golomb et al, 1987; Levy et al., 1986; Thubrikar et al., 1983; Girardot et al., 1995). Increased calcium uptake within a bioprosthesis leads to an accumulation of calcium phosphate, which in turn mineralizes into calcium hydroxyapatite. The calcification process is not well understood, but appears to depend on factors such as calcium metabolism diseases, age, diet, degeneration of tissue components such as collagen, and turbulence. Calcification of bioprostheses has been associated with degenerative changes in glutaraldehyde-treated collagen fibers.

A number of approaches have been investigated for reducing calcification of glutaraldehyde-fixed bioprostheses. For example, glutaraldehyde-fixed bioprosthetic heart valves have been treated with surfactants to reduce the calcification following implantation (U.S. Pat. No. 5,215,541). In other examples, alpha-aminooleic acid treatment of glutaraldehyde-fixed tissue has been reported as an effective biocompatible, non-thrombogenic approach for minimizing calcification of bioprosthetic devices (Girardot et al., 1991; Gott et al., 1992; Girardot et al., 1993; Hall et al., 1993, Myers et al., 1993; Girardot et al., 1994). The broad applicability of this approach in the production of bioprostheses, however, may be limited by the inability to achieve good tissue penetration of the alpha-aminooleic acid into the already glutaraldehyde-fixed tissue (Girardot, 1994).

With respect to the biocompatibility of prosthetic devices, application of most non-physiological biomaterials and prostheses to living tissues initiates a series of physiological events which can activate host defense mechanisms such as coagulation, platelet adhesion and aggregation, white cell adhesion, complement activation, etc. In attempts to improve the biocompatibility/hemocompatibility of articles adapted for use in contact with blood or blood products, aliphatic extensions have been added to the surface of polymeric biomaterials in order to provide hydrophobic binding sites for albumin. The binding of albumin to the prosthesis has been reported to provide a low activation of coagulation, low complement activation, and reduced platelet and white cell adhesion, thereby providing improved hemocompatibility (See for example U.S. Pat. No. 5,098,960; U.S. Pat. No. 5,263,992; Munro et al., 1981; Eberhart, 1989).

Some cross-linking agents have been investigated as alternatives to glutaraldehyde. These have been based on compounds such as polyepoxides, diisocyanates, di and polycarboxylic acids, photooxidation using organic dyes, etc. (see Khor, 1997, for review).

Thus, there is a need within the field of bioprosthetics for simple, cost-effective methods for cross-linking biological tissues which overcome some of the limitations associated with glutaraldehyde and other fixation approaches used in the art and which provide bioprosthetic devices with desirable mechanical characteristics and biocompatibility and a reduced susceptibility to calcification relative to glutaraldehyde-fixed tissues.

This invention broadly concerns methods for cross-linking biological tissue, and the cross-linked tissue so produced, comprising treating the tissue under effective cross-linking conditions with a compound which has an aliphatic component, typically containing from about 8 to about 40 carbon atoms, in addition to at least two chemical constituents/functionalities that are reactive with collagen. The collagen reactive groups can be essentially any chemical functionalities that are reactive with one or more of the amino acid side chains of collagen or with the collagen amide backbone. Preferred collagen reactive groups include isocyanate, epoxy, and n-hydroxysuccinimide. The aliphatic component of the cross-linking agent can be any linear or branched, saturated or unsaturated, aliphatic chain.

The disclosed invention provides an alternative approach to glutaraldehyde and other cross-linking agents for treating biological tissues, particularly those intended for use as bioprosthetic devices, and offers a number of advantages including good mechanical characteristics, biocompatibility, and a reduced susceptibility to calcification of the cross-linked tissue after implantation.

DETAILED DESCRIPTION OF THE INVENTION

A method is herein provided for cross-linking biological tissues to be used in the production of bioprosthetic devices. This is achieved by contacting a biological tissue of interest with one or more of the disclosed compounds under conditions effective to cause the desired degree of tissue cross-linking. The invention is advantageous in providing a straightforward approach for producing bioprostheses having desirable mechanical and biocompatibility features and a reduced susceptibility to calcification.

The cross-linking agents used in accordance with this invention comprise an aliphatic component, typically a linear or branched alkyl chain, and two or more chemical constituents/functionalities that are reactive with collagen. Thus, the compounds suitable for use with this invention can be generally represented by the following structural formula:

where:

$R_1$ and $R_2$ are functional groups reactive with collagen; and

X is an aliphatic chain containing from about 8 to about 40 carbon atoms.

The $R_1$ and $R_2$ endgroups of the cross-linking agents may comprise any chemical moieties that are sufficiently reactive with the collagen molecules present in the biological tissue to be treated such that the desired cross-linked tissue is formed. For example, $R_1$ and $R_2$ functional groups reactive with collagen and suitable for use in this invention can include isocyanate, epoxy, n-hydroxysuccinimide, or other collagen reactive functionalities known in the art.

The $R_1$ and $R_2$ functional groups on the cross-linking agents may be the same or different. Furthermore, they may contain or be substituted with other chemical constituents in addition to the collagen reactive groups provided they do not adversely affect the desired tissue cross-linking reaction. For example, they may contain constituents adjacent to the $R_1$ and $R_2$ end group functionalities that originate from the particular starting materials from which the $R_1$ and $R_2$ end group(s) and/or aliphatic starting materials are derived. Although such constituents would not necessarily be required for achieving the desired cross-linking of the tissues, they are nonetheless within the scope of this invention so long as they do not substantially hinder the reactivity of the cross-linking agent with the tissue.

The aliphatic chain of the cross-linking agents can be essentially any hydrocarbon chain including straight or branched, saturated or unsaturated hydrocarbons. Although the preferred aliphatic chains are most typically saturated or unsaturated hydrocarbon chains, such as alkenyl, alkenyl and alkynyl chains, other carbon containing chains are also applicable provided the desired efficacy of the cross-linking agent is not unduly compromised. The aliphatic chain may also be substituted to contain atoms in addition to carbon and hydrogen provided this does not adversely impact the efficacy of the reaction.

The mechanical properties of the fixed tissue produced in accordance with this invention can be tailored to meet the needs of a given application. For example, the number of carbon atoms present in the aliphatic chain of the cross-linking agent can influence the cross-linking density of the tissue, i.e., density will be increased with decreasing aliphatic chain length, the hydrophobicity of the tissue, and the ability of the cross-linking agent to penetrate tissue. The aliphatic chain will generally contain from about 8 to 40 carbons, preferably from about 24–40 carbons, most preferably from about 32–36 carbons.

In addition, the flexibility of the fixed tissue may be manipulated by the nature of the aliphatic chain, i.e., increased saturation of the aliphatic chain may provide a greater degree of flexibility than chains that are largely unsaturated. Thus, aliphatic chains with little or no saturation may be preferred over those with a high degree of saturation for applications where flexibility of the bioprosthesis is desired.

The cross-linking agents disclosed herein can be made using any synthetic methodologies known to the skilled individual in the art. One preferred approach involves the use of fatty acids as the source of the aliphatic chain. Fatty acids have a long aliphatic chain, typically from 12 to 20 carbons in length, and a terminal carboxylic acid group. Fatty acids can undergo a dimerization reaction by known methods to generate dimerized fatty acids having two carboxylic acid functional groups per molecule separated by an aliphatic component.

Many natural and/or commercially available fatty acids are suitable for use in producing the cross-linking agents of this embodiment, including elaidic acid, oleic acid, linoleic acid, linolenic acid, arachidonic acid and eicosapentaenoic acid and saturated fatty acids such as lauric acid, myristic acid, pentadecylic acid, palmitic acid, stearic acid and the like.

The carboxylic acid groups of fatty acids can be chemically modified, either before or after the fatty acids are dimerized, to contain the desired collagen-reactive functional groups. For example, the carboxyl groups of a dimerized fatty acid can be converted to isocyanate functionality via reductive amination and phosgenation, resulting in a bifunctional tissue-reactive cross-linking agent suitable for use in accordance with this invention. Alternatively, the carboxyl groups can be modified by any other known means provided the modification introduces the desired collagen reactivity. Reactions that can be performed at the carboxyl groups of the dimerized fatty acids are typical of those known to occur at any aliphatic carboxylic acid, i.e., esterification, amidation etc.

The biological tissue of interest is treated with one or more of the disclosed agents under conditions effective to cause the desired degree of tissue cross-linking. The skilled individual will recognize that time of treatment is not critical so long as the tissue and cross-linking agent remain in contact for a time sufficient to allow the cross-linking to occur. Time of treatment may vary depending on the type of tissue being treated and/or the particular cross-linking agent used. Typically, the length of the reaction will be from about one minute to one day or more. However, time of treatment should not be so long as to adversely effect the cross-linked tissue. Thus, cross-linking times greater than about one or two days are generally avoided. Preferably, the tissue is treated for a period from about one minute to about six hours, more preferably for about one hour to four hours. The degree of cross-linking can to some extent be varied by manipulating the length of the reaction.

A reaction temperature is selected to be effective in permitting the desired cross-linking reaction to occur while also being one that does not adversely compromise the integrity of the tissue being treated. Identification of an optimal temperature for a particular agent and/or application can be readily determined by the skilled individual. The cross-linking reaction can generally be successfully carried out at an ambient temperature, i.e., about 37 deg.C, or any other convenient temperature provided it does not exceed the tissue denaturation temperature of about 62 deg.C. Thus, a suitable reaction temperature for use in this invention may be from about 10 deg.C to about 60 deg.C, preferably from about 20 deg.C to about 50 deg.C, more preferably from about 30 deg.C to about 40 deg.C.

The tissue is treated under pH conditions that are tissue-stabilizing (i.e., which are not deleterious to the tissue being treated) and which do not adversely effect the tissue cross-linking reaction. This will typically be in a range from about pH 6 to about pH 9. More preferably, the pH will be from about 7.0 and about 8.0. Most preferably, it will be from about 7.0 to about 7.4. Optimal pH may depend to some extent on the cross-linking agent employed and/or on the tissue being treated, but can be readily determined without undue experimentation by the skilled individual in this art.

Various types of implantable biological tissues derived from numerous animal sources and parts of the anatomy can be treated in accordance with this invention. Thus, the tissue can be derived from sources such as bovine, porcine, horse, sheep, kangaroo, or rabbit, and can include such items as tendons, ligaments, heart valves, tissues used to construct heart valves such as dura mater and pericardium, etc. Other suitable tissues can include those used for augmentation such as skin patches, pericardial patches, aortic patches, tympanic membranes, etc.

In a preferred embodiment of this invention, the cross-linking agent contains isocyanate $R_1$ and $R_2$ groups and an aliphatic chain X containing from about 8 to about 40 carbons. For example, a representative compound of this type is the aliphatic diisocyantate DDI 1410™, available from Henkel (Cincinnati, Ohio). This compound is based on a dimerized fatty acid containing 36 carbon atoms wherein the carboxyl groups of the dimer have been modified so as to introduce isocyanate groups. This compound has good flexibility, a high degree of hydrolytic stability and is highly reactive with collagenous tissue.

The process of cross-linking biological tissues can be carried out in any suitable solvent. Choice of solvent is generally not critical, however, preferred solvents will typically be water-miscible, will have minimal toxicity to the tissue and/or the recipient, will be non-denaturing, and will be compatible with the collagen cross-linking reaction. Some such solvents include, but are not limited to, linear or branched lower alcohols (i.e., having from about one to four carbons); aprotic high polarity organic solvents such as n-methyl pyrrolidinone, dimethylsulfoxide etc.; lower ketones (i.e., having from about 3 to 6 carbons) such as methyl ethyl ketone or cyclohexanone; and polyhydroxy compounds such as glycerol, ethylene glycol, or polyethylene glycols having molecular weights less than about 1000. When using the described isocyanate-containing cross-linking agents of the invention, the reaction is preferably carried out under anhydrous conditions in order to circumvent the high reactivity of the isocyanate to water.

The cross-linking agents of this embodiment, by virtue of their two isocyanate functionalities, are bi-functional and can react with collagen at side groups containing, for example, hydroxyl, amine, amide, carboxylic acid and thiol functionalities. Such agents are advantageous in being reactive with collagen at ambient temperatures without the need for catalysts, they exhibit a high degree of hydrolytic stability, have significantly lower toxicity compared to small molecule diisocyanates (LD 50 g/kg, acute oral rat>34.5, acute dermal rabbits>23.1), and can improve biocompatibility and reduce calcification of the bioprostheses so produced.

EXAMPLES

Fatty acid based diisocyanate (DDI 1410™) was obtained from Henkel Corporation (Cincinnati, Ohio). All other chemicals used were of reagent grade and were purchased from standard suppliers such as Aldrich (Milwaukee, Wis.), Fluka (Ronkonkoma, N.Y.) and Sigma (St. Louis, Mo.).

Fresh bovine pericardium tissue samples stored in chilled PBS (phosphate buffered saline) were cut into several 1 cm×1 cm pieces. The cut pieces were gently wiped using clean tissue paper to remove excess water. The cut pieces were then transferred into 20 ml glass scintillation vials containing DDI 1410. The chemical composition and amount for each treatment is reported in Table 1. The tissue was removed from the vial after 16 hours treatment at ambient temperature and was washed twice with 2.5 ml hexane to remove unreacted DDI 1410. The treated tissue was stored in 50% ethanol or a 50% alcohol/HSHS (high salt-high sugar) solution for further analysis.

Shrink temperature and polyacrylamide gel electrophoretic analysis of tissue extracts were performed to confirm the cross-linking of bovine pericardium using fatty acid based derivatives. The shrinkage temperature was determined using standard differential scanning calorimetric analysis. Briefly, 2–10 mg of tissue was heated at 10° C. under nitrogen atmosphere. The endotherm around 60–80° C. is typically referred as shrinkage temperature. The onset temperature is used as shrinkage temperature. An increase in the shrinkage temperature using this approach is an indication that tissue cross-linking has occurred.

Protein extraction assays were determined as follows. Briefly, 10–20 mg of tissue was extracted with 10–20 microliter extraction solution containing 50 mM Tris-HCl (pH 6.8), 10% glycerol, 4% mercapto ethanol, 1% sodium dodecyl sulfate, 0.5M sodium chloride, and 0.01% bromophenol blue. The extracted solution was then analyzed on a 4–20% acrylaminde:bisacrylamide (37.5:1 Mini-PROTEAN II ready Gel (Biorad, Richmond, Calif.). Cross-linking results in less extractable protein from biomaterial.

For these experiments, neat liquid DDI1410 or solutions of DDI 1410 in hexane or isopropanol were used. Hexane is a solvent for DDI 1410 and is immiscible in water. The hexane solutions had lower viscosity as compared to neat DDI 1410. Isopropanol is soluble in water as well as in DDI 1410. Photooxidized, lyophilized and ethylene oxide treated bovine pericardium tissue samples were treated with neat DDI 1410 liquid.

The results of these experiments are summarized in Table 2. The control/untreated sample had a shrinkage temperature of 63.9° C. This is a typical value for untreated bovine pericardium tissue. The viscosity of DDI 1410 was reduced by adding hydrophobic hexane as a solvent. The hexane solution treated tissue had a shrinkage temperature of 64.45° C., indicating that no substantial cross-linking had occurred. This failure to induce cross-linking may be attributed to the hydrophobicity of DDI 1410 and hexane. Tissue treated with DDI 1410 dissolved in isopropanol had a shrinkage temperature 75.76° C. indicating that substantial cross-linking had been achieved. When the tissue was treated with neat DDI 1410 liquid, the shrinkage temperature was 73.55° C. This tissue sample was washed with isopropanol before treatment. Thus, the water solubility of isopropanol may provide for greater penetration of DDI 1410 within the tissue, resulting in better cross-linking of the tissue. The removal of water from the tissue by lyophilization and subsequent treatment with neat DDI 1410 did not alter the shrinkage temperature.

The results of an electrophoresis extraction assay were analogous to the shrinkage temperature results. The isopropanol treated tissue sample showed substantial reduction in extractable proteins indicating cross-linking of the tissue.

TABLE 1

| Sample | Treatment |
| --- | --- |
| Control | No treatment, Sample in PBS buffer |
| Hex + DDI | Tissue treated with 1.5 ml hexane and 1.5 ml DDI 1410 |
| IP + DDI | Tissue treated with 1.5 ml isopropanol and 1.5 ml DDI 1410 |
| DDI-EO | Photooxidized tissue, lyophilized and sterilized with ethylene oxide is treated with 1.5 ml DDI 1410 |
| DDI neat | Tissue washed with isopropanol (5 ml × 3) and treated with 2 ml DDI 1410 |
| EO-control | Photooxidized tissue, lyophilized and sterilized with ethylene oxide, no treatment |

TABLE 2

| Sample Code | Protein Extraction Assay | Shrinkage Temperature (° C.) |
| --- | --- | --- |
| Control | Extractable proteins present | 63.95 |
| Hex + DDI | Extractable proteins present, reduced | 64.44, 117.48 |
| IP + DDI | Extractable proteins present, substantially reduced | 75.76 ± 1.20 |
| DDI-EO | Extractable proteins present, substantially reduced | 61.45 |
| DDI neat** | Extractable proteins present, reduced | 73.55 |
| EO-control | Extractable proteins present, substantially reduced | 62.37 |
| Glutaraldehyde fixed* | Extractable proteins present, substantially reduced | 86.1 ± 0.5 |

**Tissue washed with isopropanol prior to treatment

REFERENCES

The following references, to the extent that they provide exemplary procedural or other details supplementary to those set forth herein, are specifically incorporated herein by reference.

Broom, J Biomech (1977) 10:707–727
Eberhart, IEEE Eng in Med and Bio (June 1989) p26
Gendler et al., J Biomed Mater Res (1984) 18: 727–736
Girardot et al., Trans Soc Biomat (1991) 14:114
Girardot et al., Trans Soc Biomat (1993) 16:266
Girardot et al., Int J Artif Org (1994) 17: 76
Girardot et al., J Biomed Mater Res (1995) 29: 793–801
Golomb et al., Am J Pathol (1987)127: 122–130
Gott et al., Ann Thorac Surg (1992) 53: 207
Hall et al., ASAIO Proc (1993): 24
Khor, Biomaterials (1997) 18: 95–105
Levy et al, In: Williams D F, ed. CRC Critical Rev. in Biocompatibility, Vol. 2 (1986): 147–187.
Magilligan, Trans Am Soc Artif Intern Organs (1988) 34: 1031–1032
Moczar et al., ASAIO J (1994) 40: M697–M701
Munro et al, Trans Amer Soc Artif Intern Organs (1981) 27: 499–503
Myers et al., Int J Artif Org (1993) 16: 453
Thubrikar et al., J Thorac Cardiovasc Surg (1983) 86: 115–125
Wiebe et al., Surgery (1988) 104: 26–33

What is claimed is:

1. A method for cross-linking collagen-containing biological tissue comprising treating the tissue under effective cross-linking conditions with a compound having the formula $R_1$-X-$R_2$ where $R_1$ and $R_2$ are functional groups reactive with collagen and X is a $C_8$ to $C_{40}$ aliphatic chain.

2. The method of claim 1, wherein $R_1$ and $R_2$ are selected from the group consisting of isocyanate, epoxy and n-hydroxysuccinimide.

3. The method of claim 1, wherein X is a $C_{24}$–$C_{40}$ aliphatic chain.

4. The method of claim 1, wherein X is derived from a dimerized fatty acid.

5. The method of claim 4, wherein the fatty acid is selected from the group consisting of elaidic acid, oleic acid, linoleic acid, linolenic acid, arachidonic acid, eicosapentaenoic acid, lauric acid, myristic acid, pentadecylic acid, palmitic acid and stearic acid.

6. The method of claim 1, wherein the tissue is derived from human, bovine, porcine, horse, sheep, or rabbit.

7. The method of claim 1, wherein the tissue comprises a tissue of a tendon, ligament, heart valve, dura mater, pericardium, skin patch, pericardial patch, aortic patch or tympanic membrane.

8. The method of claim 1, wherein the tissue is treated in a solvent selected from the group consisting of $C_1$–$C_4$ alcohols, $C_3$–$C_6$ ketones, and polyhydroxy compounds having molecular weights less than about 1000.

9. The method of claim 1, wherein the tissue is treated in a solvent selected from the group consisting of isopropanol, methyl ethyl ketone, cyclohexanone, glycerol, ethylene glycol, n-methyl pyrrolidinone, and dimethylsulfoxide.

10. The method of claim 1, wherein the tissue is treated at a pH of from about 6 to about 9.

11. The method of claim 1, wherein the tissue is treated at a pH of from about 7 to about 8.

12. The method of claim 1, wherein the tissue is treated for a period of from about 1 minute to about 6 hours.

13. Cross-linked biological tissue produced according to the method of claim 1.

14. A method for cross-linking collagen-containing biological tissue comprising treating the tissue under effective cross-linking conditions with a compound having the formula OCN—X—NCO where X is a $C_8$ to $C_{40}$ aliphatic chain.

15. The method of claim 14, wherein X is derived from dimerized fatty acids.

16. The method of claim 15, wherein the fatty acid is selected from the group consisting of elaidic acid, oleic acid, linoleic acid, linolenic acid, arachidonic acid, eicosapentaenoic acid, lauric acid, myristic acid, pentadecylic acid, palmitic acid and stearic acid.

17. The method of claim 14, wherein X is a $C_{36}$ aliphatic.

18. The method of claim 14, wherein the tissue is derived from human, bovine, porcine, horse, sheep, or rabbit.

19. The method of claim 14, wherein the tissue comprises a tissue of a tendon, ligament, heart valve, dura mater, pericardium, skin patch, pericardial patch, aortic patch or tympanic membrane.

20. The method of claim 14, wherein the tissue is treated in a solvent selected from the group consisting of $C_1$–$C_4$ alcohols, $C_3$–$C_6$ ketones, and polyhydroxy compounds having molecular weights less than about 1000.

21. The method of claim 14, wherein the tissue is treated in a solvent selected from the group consisting of isopropanol, methyl ethyl ketone, cyclohexanone, glycerol, ethylene glycol, n-methyl pyrrolidinone, and dimethylsulfoxide.

22. The method of claim 14, wherein the tissue is treated at a pH of from about 6 to about 9.

23. The method of claim 14, wherein the tissue is treated at a pH of from about 7 to about 8.

24. The method of claim 14, wherein the tissue is treated for a period of about 1 minute to about 6 hours.

25. Cross-linked biological tissue produced according to the method of claim 14.

* * * * *